C. W. THORNTON.

SANITARY CLEANSING AND INDICATING DEVICE FOR DRINKING VESSELS.

APPLICATION FILED MAR. 4, 1911.

Reissued Aug. 8, 1911.

13,280.

2 SHEETS—SHEET 1.

Witnesses
Frank P. Glore
H. L. Rodgers.

Inventor
C. W. Thornton
By Georgy Thorpe Atty.

COLUMBIA PLANOGRAPH CO., WASHINGTON, D. C.

C. W. THORNTON.

SANITARY CLEANSING AND INDICATING DEVICE FOR DRINKING VESSELS.

APPLICATION FILED MAR. 4, 1911.

Reissued Aug. 8, 1911.

13,280.

2 SHEETS—SHEET 2.

Witnesses
Frank R. Fox.
H. L. Rodgers.

Inventor
C. W. Thornton

By George H. Thorpe Atty.

COLUMBIA PLANOGRAPH CO., WASHINGTON, D. C.

UNITED STATES PATENT OFFICE.

CHARLES W. THORNTON, OF DALHART, TEXAS, ASSIGNOR OF ONE-TENTH TO JOSEPH L. WILLIAMS, OF TEXHOMA, TEXAS.

SANITARY CLEANSING AND INDICATING DEVICE FOR DRINKING VESSELS.

13,280. Specification of Reissued Letters Patent. Reissued Aug. 8, 1911.

Original No. 959,970, dated May 31, 1910, Serial No. 541,660. Application for reissue filed March 4, 1911. Serial No. 612,411.

*To all whom it may concern:*

Be it known that I, CHARLES W. THORNTON, a citizen of the United States, and resident of Dalhart, in the county of Dallam and State of Texas, have invented certain new and useful Improvements in Sanitary Cleansing and Indicating Devices for Drinking Vessels and the Like, of which the following is a specification.

My invention relates to apparatus or means for cleansing vessels and at the same time indicating which vessel has been cleansed; and the object is to provide devices for cleansing or sterilizing vessels, particularly drinking vessels in public places, such as public drinking fountains, drinking cups on railway trains, and other places, and in a striking manner or determining manner warning the person which vessel has been cleansed.

The object of such provision is to prevent spread of disease by washing a vessel in some antiseptic solution after the vessel has been used by an afflicted person.

Other objects and advantages will be fully explained in the following description and the invention will be more particularly pointed out in the claims.

Reference is had to the accompanying drawings which form a part of this application.

Figure 1:
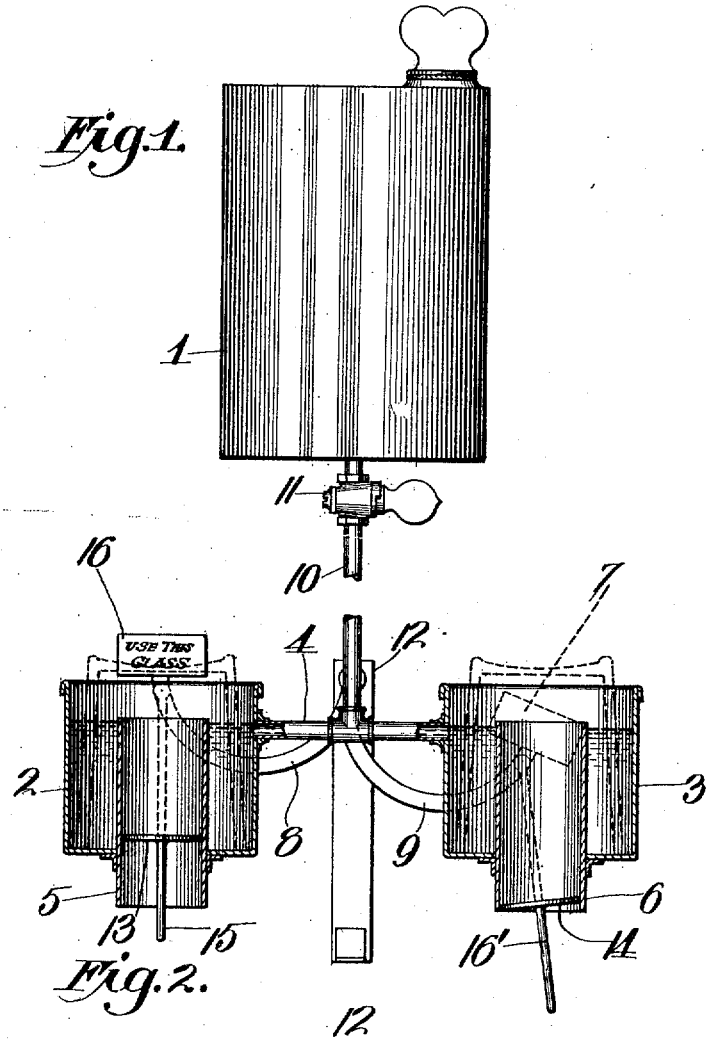
Figure 2:
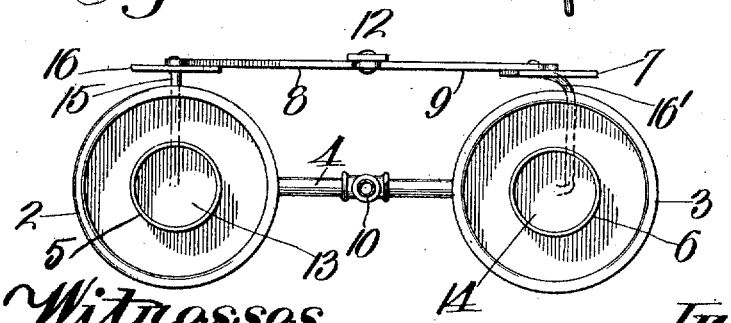
Figure 3:
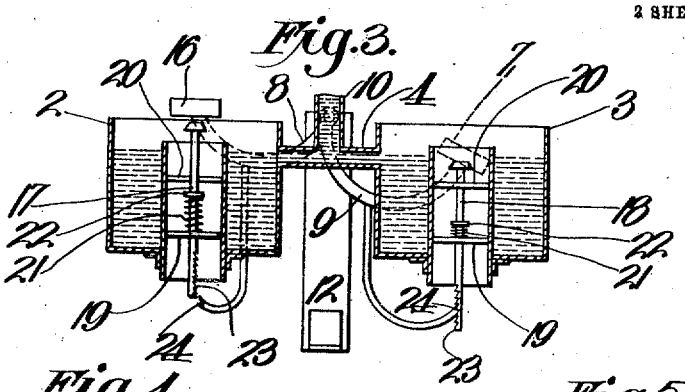
Figure 4:
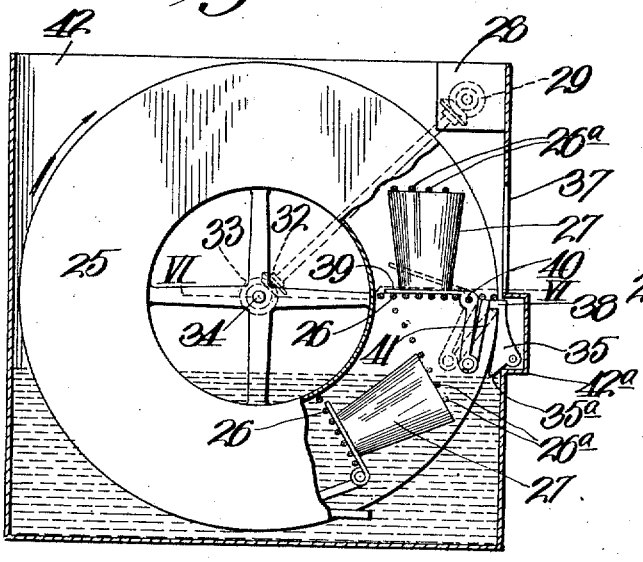
Figure 5:
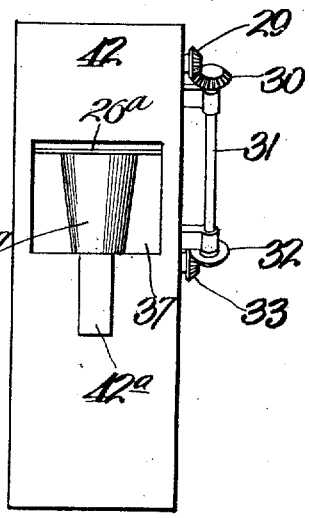
Figure 6:
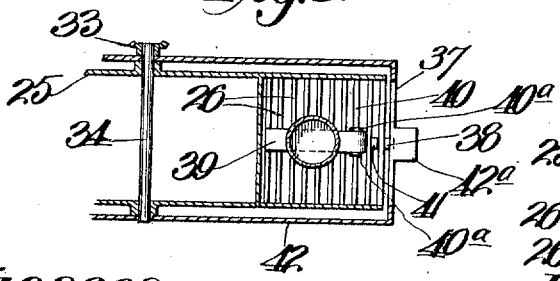
Figure 7:
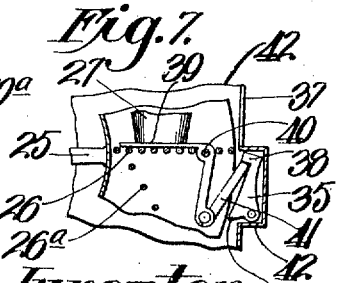

Figure 1, is a vertical section of the cleansing apparatus, the tank containing the supply of antiseptic solution being shown in side elevation. Fig. 2, is a plan view of the cleansing apparatus. Fig. 3, is a central section illustrating a modified form of the indicating mechanism. Fig. 4, is a view of a different form of apparatus, the view showing the solution containing casing or tank in vertical section, a rotary glass carrier partly in elevation and partly in section, means for operating the carrier or wheel, and means for arresting the carrier or wheel at predetermined points. Fig. 5, is an edge view of the construction illustrated by Fig. 4. Fig. 6, is a horizontal section on the line VI—VI of Fig. 4. Fig. 7, is a fragmentary section showing the carrier or wheel arresting mechanism in tripped position to permit the carrier or wheel to rotate.

Similar characters of reference are used to indicate the same parts throughout the several views.

The apparatus for carrying out the objects of this invention includes a tank 1 for containing an antiseptic solution. Below the tank are mounted devices for cleaning two drinking glasses or other vessels. Two cleaning vessels 2 and 3 are connected by a tube 4 so that a cleansing liquid will stand normally at the same level in both vessels or receptacles. These receptacles are open top receptacles and tubes 5 and 6 are mounted centrally in the receptacles and extended below the receptacles and extended near the tops of the vessels. Glasses or drinking vessels are to be inverted and placed down on the tubes 5 and 6 to be cleansed, as shown by dotted lines Fig. 1. Means are provided for indicating which glass or drinking vessel has been cleansed and ready for use. Signs 16 and 7 are provided to be automatically actuated by the insertion of the glasses. The signs 16 and 7 are mounted on arms 8 and 9 which are rigid with each other. The vessels 2 and 3 are connected to the tank 1 by a tubular neck 10 which is provided with a cut-off cock 11. The arms 8 and 9 are pivotally mounted in a support 12. Movable platforms 13 and 14 are mounted within the tubes 5 and 6 and are supported on arms 15 and 16′ which are pivotally connected to the arms 8 and 9 respectively. The platforms 13 and 14 are or should be almost as large in area as cross-sections of the tubes 5 and 6.

The action is as follows: When a glass is placed on the tube 5, it will descend into the solution in the vessel 2 by gravity and will force liquid over the top of the tube 5 to fall on the platform 13 and enough liquid will fall on the platform 13 to cause the sign 16 to descend and the sign 7 will be forced upwardly into view. The signs 16 and 7 and the arms and connections which carry these signs should be made respectively equal to each other so that a small quantity of liquid will change the balance and cause the operation of the signs. The signs may have such words as "Use this glass" or similar words or words having similar meaning printed or made thereon. The apparatus thus described will cause alternate use of the glasses. The liquid in the receptacles 2 and 3 will be thrown out gradually, but the supply will be automatically obtained from the tank 1. As soon as the liquid in tube 4 falls below the mouth of the neck 10, air will enter the neck 10 and the tank 1 and liquid will run down until the mouth of the neck is again closed. This action will occur as often as the liquid in the tube 4 becomes lower than the mouth of neck 10. The operation of the apparatus described will be a safeguard against a person using a glass until it has been sterilized.

Fig. 3 of the drawing shows a variation in the means for operating the sign instead of the platforms 13 and 14 shown in Figs. 1 and 2. Spring-actuated rods 17 and 18 are mounted in the tubes 5 and 6 by means of cross bars 19 and 20 and spiral springs 21 are mounted on the rods 17 and 18 between the bars 19 and collars 22. The springs 21 will normally hold the rods 17 and 18 in elevated position but when a glass is inverted over one of the rods it will press the rod down and actuate the sign in the opposite part of the apparatus. Each rod 17 and 18 has a rack 23 on the lower end thereof which rack is adapted to engage a spur 24. When the rack 23 of rod 18 engages the spur 24 it will pull the arm 9 downwardly and elevate the arm 8. The rod 17 will in the same manner elevate the arm 9 and consequently the sign carried by the arm. The spurs 24 are carried by rods similar to the rods 15 and 16′ which are pivotally connected to the arms 8 and 9.

In the modification or variation illustrated in Figs. 4, 5, 6 and 7, 42 is a casing provided with an opening 37 in one end wall. If of sheet metal as shown, the casing will preferably be provided with an offset 42ª for a purpose which hereinafter appears. Within the casing and partially submerged by the antiseptic solution therein contained, is a wheel 25 shown with a peripheral groove or channel divided into compartments by partitions 26 preferably of wire as shown, each compartment being adapted to contain a drinking glass 27 and each compartment is preferably provided with a wire partition 26ª for engagement with the top of its respective glass so as to hold the latter reliably in place. Clockwork gearing may be utilized to revolve the wheel or carrier 25, and this gearing is inclosed in the casing 28 secured within casing 42, and actuates a bevel gear wheel 29 meshing with a bevel gear wheel 30 mounted on a suitably journaled shaft 31. The shaft 31 is equipped at its inner end with a bevel gear 32, meshing with a bevel gear 33 mounted on a shaft 34 which carries the wheel 25 and is journaled in the casing in any suitable manner. The clock gearing may be wound up as any clock is wound and tends to revolve the wheel 25 continuously in the direction indicated by the arrow.

Provision is made for locking the wheel 25 against rotation when not in use. A dog 35 is pivotally mounted on casing 42 within the offset 42ª thereof so as to be out of sight and reach. The dog tends to swing inwardly or toward the wheel and is limited in such movement when otherwise unopposed by the extension 35ª which strikes against the casing as shown in Fig. 4. The inward movement of the dog disposes its upper end or tooth 38 in the path of partition 26, so that the dog shall arrest the wheel as each partition of the same encounters it, the parts being so proportioned and arranged that when the partition is in engagement with the dog, the glass in the compartment above said partition will be observable through the opening 37 so that one desiring to use the glass may reach into the casing, withdraw the glass and after using it replace it in its original position, the wheel remaining stationary until the glass is replaced.

39 is a bell crank lever pivoted on one of the wires of each partition, the particular wheel wire being indicated by the reference character 40 and to prevent lateral movement of the lever collars 40ª are secured on said wire at opposite sides of the lever. The upper arm of the lever overlies the partition wires and is held down upon said wires by the glass when in position, the other arm of the lever depends into the space between said partitions and the underlying partition 26ª, and pivoted to the lower end of said depending arm of the lever is an upwardly projecting pawl, any suitable connection such as a rule-joint connection serving to limit the outward swinging of the pawl 41 from the lever, the limit of such separating movement being shown in Fig. 7.

Just before the wheel is arrested, the pawl 41 at such time observable through opening 37 comes in contact with the tooth of dog 35 and offering the least resistance to pivotal movement, is pushed inwardly by said tooth to the position shown in Fig. 4, and as it attains such position, the outermost wire of the adjacent partition 26 strikes upon the upper side of the tooth, this engagement resulting in the arrest of the wheel with the parts in the position shown by full lines Fig. 4. If a person removes the glass the bell crank lever and pawl assume the position shown in dotted lines same figure, the pawl being of sufficient weight to effect this adjustment, it being noted that the free end of the pawl drops down under the tooth 38 of the dog. As the glass is replaced, the lever is rocked back to its original position and the pawl is caused to reverse the dog as shown clearly in Fig. 7. As the operator releases the glass the clock work starts the wheel on its travel that said partition shall attain a position in the path of or below the tooth of the dog to prevent the latter arresting the rotation until the corresponding wire of the following partition engages it in the manner explained, all subsequent operations being repetitions of those described.

From the foregoing it will be apparent that the glasses are successively passed through the solution standing in the tank and that each is allowed sufficient time for drainage between the time of emerging from the solution and attaining a position where it is accessible through opening 37.

The vessels 2 and 3 have been described as separate vessels, but it is apparent that the two vessels can be constructed as one vessel and that additional provision may be made therein for immersing additional drinking vessels to be indicated by additional signs.

Having fully described my invention, what I claim as new and desire to secure by Letters Patent, is:—

1. An automatic cleaning and indicating apparatus comprising a solution containing receptacle, provision in said receptacle for immersing vessels in said solution, and indicating devices automatically actuated by the immersing of one vessel in said solution to show which vessel has been cleansed.

2. An automatic cleansing apparatus comprising solution holding members, means for holding vessels to be cleansed in said solution, and means for indicating which vessel has been cleansed.

3. An automatic cleansing and indicating apparatus comprising solution holding devices, vessel-holding members in said solution, and automatically actuated indicating devices to indicate which vessel has been cleansed.

4. An automatic cleansing and indicating apparatus comprising a pair of solution containing receptacles, open vertical tubes mounted in said receptacles and projecting through the bottoms thereof, a pair of arms pivotally mounted, signs carried by said arms, and platforms movable vertically in said tubes and operatively connected with said arms.

5. An automatic cleansing and indicating apparatus comprising a plurality of solution containing receptacles, an open vertical tube mounted in each receptacle and projecting through the bottom thereof, a sign for use with each tube, and platforms movable vertically in said tubes and each platform being operatively connected with one of said signs.

6. An automatic cleansing and indicating apparatus comprising a plurality of solution containing receptacles, an open vertical tube mounted in each receptacle and projecting through the bottom thereof, a sign for use with each tube, platforms movable vertically in said tubes, and each platform being operatively connected with one of said signs, the platform of one tube being operatively connected with the sign of the opposite tube, and a tank operatively connected with said receptacles for automatically replenishing the solution in said receptacles.

7. A cleansing apparatus, comprising a solution-containing vessel, a tube extending into the vessel to a point above the level of the solution, through which solution may be caused to escape from the receptacle by the insertion of a drinking vessel in the latter to raise the level of the solution until it overflows said tube, and means for automatically replenishing the receptacle with additional solution when the level of the original charge of solution therein falls through the removal of the drinking vessel.

8. A cleansing apparatus, comprising a solution-containing vessel, a tube extending into the vessel, with its end therein disposed above the level of the solution and spaced from the wall of the vessel so as to be received within a drinking vessel inserted in inverted position into the receptacle and adapted when so inserted to cause a quantity of the solution to overflow and escape from said tube, and means for automatically replenishing the receptacle with additional solution when the level of the original charge of solution falls through the removal of the drinking vessel.

9. A cleansing apparatus, comprising a vessel, a tube extending upward through the bottom of the vessel, a tube communicating with the vessel through the side thereof in substantially the plane of the upper end of the tube extending through the bottom of the vessel, so that the insertion of a glass into the vessel around the tube extending through the bottom of the vessel shall cause sufficient solution to overflow said tube to admit air into the tube communicating with the vessel through the side thereof, and means for automatically supplying solution to the vessel through the last-named tube as air enters the same.

In testimony whereof I affix my signature in the presence of two witnesses.

CHARLES W. THORNTON.

Witnesses:

FRANK R. GLORE,
G. Y. THORPE.

Copies of this patent may be obtained for five cents each, by addressing the "Commissioner of Patents, Washington, D. C."